United States Patent [19]
Yang et al.

[11] Patent Number: 5,516,520
[45] Date of Patent: May 14, 1996

[54] CONTROLLED-RELEASE PESTICIDES AND METHODS FOR PREPARATION AND USE THEREOF

[75] Inventors: Chien-Chun Yang, Hsinchu; Suey-Sheng Kao; Ching-Chou Tzeng, both of Taipei; Mei-Hueih Chen, Hsinchu, all of Taiwan

[73] Assignee: Industrial Technology Research Institute, Taiwan

[21] Appl. No.: 253,592

[22] Filed: Jun. 3, 1994

Related U.S. Application Data

[63] Continuation of Ser. No. 923,417, Jul. 31, 1992, abandoned.
[51] Int. Cl.$^6$ ..................... A01N 25/12
[52] U.S. Cl. ............ 424/408; 424/405; 424/418; 424/493
[58] Field of Search .................... 424/405, 408, 424/488, 493, 418

[56] References Cited

U.S. PATENT DOCUMENTS 4,439,488  3/1984  Trimnell et al. ................ 428/402.24

OTHER PUBLICATIONS

Kirk–Othmer (1985) "Concise Encyclopedia of Chemical Technology", John Wiley & Sons, publishers; New York, USA, pp. 652–656.

Felix H. Otey, et al. (1984) *J. Agriculture Food Chemistry*, vol. 32, pp. 1095–1098.

D. Trimnell, et al. (1982) *J. Applied Polymer Science*, vol. 27, pp. 3919–3928.

B. S. Shasha, et al. (1984) *J. Applied Polymer Science*, vol. 29, pp. 67–73.

B. S. Shasha, et al. (1989), *J. Controlled Release*, pp. 255–257.

B. S. Shasha, et al. (1981) *J. Polymer Science*, vol. 19, pp. 1891–1899.

*Primary Examiner*—Thurman K. Page
*Assistant Examiner*—Neil Levy
*Attorney, Agent, or Firm*—Darby & Darby

[57] ABSTRACT

A particulate controlled-release pesticide composition having a pesticide encapsulated in a polymer matrix of starch-borax-urea and method of preparation and use thereof is provided. The release rates and release duration of the pesticide compositions are controllable by adjusting the urea content in the compositions. The pesticide composition is preparable by admixing starch, pesticide, urea and water together to form a mixture and agitating the same at a temperature sufficient to gelatinize the mixture and to disperse the mixture. Borax is then added to the mixture in an amount effective to convert the mixture into a rubbery mass. The rubbery mass is then comminuted into small particles, in the presence of added starch, and dried.

3 Claims, No Drawings

CONTROLLED-RELEASE PESTICIDES AND METHODS FOR PREPARATION AND USE THEREOF

This is a continuation of application Ser. No. 07/923,417, filed Jul. 31, 1992 now abandoned.

FIELD AND BACKGROUND OF THE INVENTION

Pesticides are employed in agriculture to improve crop yields by controlling pests such as weeds, insects, nematodes and fungi which attack plants and transmit diseases. Pests result in an estimated total annual loss to U.S. agriculture of about 10% of production, and an estimated worldwide agricultural losses of about 14% of production. Pesticides, however, require repeated application at targeted sites during the growing season to replace losses due to volatilization, leaching and degradation. Repeated pesticide application, however, is undesirable because of high costs and possible phytotoxicity, and because certain pesticides are well known environmental pollutants. For a review on pesticides, see, Kirk-Othmer's "Concise Encyclopedia of Chemical Technology," John Wiley & Sons, publishers; New York, USA, 1985, pages 652–656.

Various pesticide compositions and methods for preparing the same have been developed in attempt to enhance pesticidal efficacy so that less pesticide may be used and to reduce the need for repeated application. Exemplary of such compositions include controlled-release pesticide formulations which has become increasingly popular due to safe handling and ease of application.

Conventional controlled-release formulations typically employ natural or synthetic polymers to uniformly disperse and encapsulate the pesticides. These formulations, however, suffer from a number of deficiencies which include ineffective control of the released amount of pesticide per unit time and control of the duration of the release period. Moreover, the compositions are suitable for encapsulating a limited number of pesticides. Accordingly, there is a need in the art for improved controlled released pesticide formulations which overcome one or more of the aforementioned deficiencies.

B. S. Shasha et al. ((1981) *J. Polymer Science, Polymer Chemistry Edition,* Vol. 19, pages 1891–1899) disclose encapsulation of oil soluble pesticides in a starch-calcium matrix by mixing the pesticides with alkali starch followed by precipitation of the mixture with a calcium chloride solution. D. Trimnell et al. ((1982) *J. Applied Polymer Science,* Vol. 27, pages 3219–3928) describe oil soluble pesticide encapsulation using a starch-borate complex by mixing starch, pesticide, and water to form a mixture; adding alkali to the mixture gelatinize the starch; and boric acid treatment of the gelatinized mixture. These methods, however, are not suitable for encapsulating pesticides which are alkali-sensitive. Moreover, the methods do not provide controlled release formulations having selective release rates of pesticides at the same pesticide loading.

B. S. Shasha et al. ((1984) *J. Applied Polymer Science,* Vol. 29, pages 67–73) studied herbicide S-ethyl dipropylthiocarbamate (EPTC) encapsulation in a starch-borate complex. The method involves mixing the herbicide into a neutral paste of pregelatinized starch or flour, followed by the addition of ammonia or an amine. The paste is subsequently treated with boric acid or borate salt to form a gel, which is then coated with additional starch to facilitate breaking of gel into particles for drying. While satisfactory yields of encapsulated products are obtainable from these methods, Shasha does not suggest any method for selectively controlling the pesticide release rate of the encapsulated products at the same pesticide loading.

F. H. Otey et al. ((1984) *J. Agriculture and Food Chemistry,* Vol. 32, pages 1095–1098) describes the use of a starch or starch-borate matrices for controlled release of urea fertilizer. B. S. Shasha et al. ((1989) *J. Controlled Release,* Vol. 19, Page 255) described urea pellets coated with starch containing entrapped herbicides. These papers, however, do not disclose nor suggest a method for encapsulating pesticides or a controlled-release pesticide composition having selective release rate properties.

Accordingly, there is a need in the art for improved controlled-release formulations for encapsulating a broad range of oil-soluble pesticides and which have controllable release rates and release periods, relative to conventional formulations, and a practical method for preparing the same.

SUMMARY OF THE INVENTION

The present invention provides an improved controlled-release pesticide formulation comprising a pesticide encapsulated in a polymer matrix of starch-borax-urea. The invention also provides a method for preparing the improved pesticide formulation so that pesticide release rate and release period are adjustable to any desired suitable level depending the pesticide type, the target site, and extent of pest infestation.

According to the method of the present invention, an oil soluble pesticide, starch, and water in suitable ratios are admixed. Thereafter, urea is added to the mixture to gelatinize the starch. The mixture is then blended at high speed until the temperature reaches 60°–80° C. to thoroughly disperse the pesticide in the starch gel. Borax is then mixed into the dispersed mixture in an amount sufficient to convert the mixture into a rubbery mass. The rubbery mass is then ground, under high-speed and in the presence of additional starch powder, into small starch-coated particles which are then dried.

DETAILED DESCRIPTION OF THE INVENTION

All patents, patent applications and literature references cited in this specification are hereby incorporated by reference in their entirety.

The present invention is based on the discovery that pesticide formulations having controllable release rates and periods, at the same pesticide loading, can be prepared by encapsulating the pesticide in a starch-borax-urea matrix. The controlled release pesticide formulation are manufactured by admixing starch powder, pesticides, urea and water in suitable ratios and dispersing the mixture at a temperature ranging between about 60° C. and about 80° C. to gelatinize the starch and to thoroughly and uniformly disperse the pesticide in the gelatinized starch. Borax is mixed into the gelatinized mixture to convert the mixture into a rubbery mass. The mass is then comminuted, in the presence of added starch powder, into small particles.

The release rate and release period of the formulations are adjustable by varying the urea content in the mixture. At increasing urea concentrations in the mixture, pesticide formulations having decreasing pesticide release rates and longer durations are obtainable. Urea serves to gelatinize the starch in the mixture and is releasable from these particles, hence providing an added fertilizing effect for the pesticide formulations of the present invention.

In practicing the invention, a starch, pesticide and water mixture is prepared, at room temperature, by mixing starch powder in an amount ranging between about 35 and about 41 wt. %, preferably between about 38 and about 40 wt. % of the mixture; pesticide in an amount ranging between about 1.0 and about 12.5 wt. % preferably between about 3 and about 10 wt. % of the mixture; and water in an amount ranging between about 45 and about 60 wt. %, preferably between about 48 and about 55 wt. % of the mixture. Urea is then added to the mixture to gelatinize the starch.

It will be understood by the skilled practitioner that the amount of urea added to the mixture depends on the desired release properties for final pesticide formulation. In practicing the invention, suitable amounts of urea in the mixture range broadly between about 4 and about 25 wt. %, preferably about 8 and about 20 wt. % of the mixture.

Suitable, but non-limiting, examples of oil-soluble pesticides for use in the invention include allethrin, deltamethrin, permethrin, cypermethrin, chlorpyrifos and diazinon. A particularly suitable pesticide for use in the invention is deltamethrin. It will be understood that one or more pesticides can be incorporated into the pesticide composition of the present invention. The selection of a suitable pesticide(s) will depend the type of pest sought to be controlled or eliminated.

Suitable, but non-limiting, examples of starch powder include starch derived from potato, corn, tapioca, and barley. A preferred starch for use in the invention is tapioca starch.

The mixture is then agitated, e.g, with a Waring blender set at high speed, at a temperature ranging between about 60° and about 80° C., preferably between about 68° C. and about 76° C., for a period of time sufficient to complete the gelatinization process and to thoroughly and uniformly disperse the pesticide in the mixture. The dispersion process is generally performed for a period of time of about 15 minutes or longer. Heat is usually generated during the blending process or may be supplied by external sources, e.g. preheating the mixture in an bath or oven.

Thereafter, borax (sodium borate) is added to the dispersed mixture in an amount sufficient to convert the mixture into a uniform rubbery mass. A suitable amount of borax ranges broadly between about 4 and about 7 wt. %, preferably between about 4.5 and about 6 wt. % of the mixture.

The mass is then ground, e.g. with a Waring blender, into small particles in the presence of added starch powder, at a speed ranging between about 600 and about 3000 rpm, preferably between about 1000 and about 2000 rpm, for a time period ranging between about 10 and about 15 minutes at a temperature ranging between about 20° C. and about 50° C., preferably about 40° C.

The amount of added starch powder generally ranges between about 20 and about 39 wt. %, preferably between about 25 and about 35 wt. % of the mixture.

The resultant starch-coated particles have a particle mesh size ranging between about 16 and about 90. These particles are subsequently dried at a temperature ranging between about 50° C. and about 60° C., preferably about 60° C., for a time period sufficient to reduce the water content of the particles to levels of about 10 and about 15 wt. %. Generally, the drying process is performed for a period of time ranging between about 18 and about 24 hours.

The dried particles obtained by the method of the present invention generally have a particle mesh size ranging between about 10 and about 60, preferably about 16 and about 40. The water content of the dried particles generally range between about 10 and about 15 wt. %, preferably about 12 wt. %.

The dried particles have a pesticide content ranging between about 1 and about 12.5 wt. %, preferably about 8 wt. %; a starch content ranging between about 50 and about 80 wt. %, preferably about 75 wt. %; a urea content ranging between about 4 and about 25 wt. %, preferably between about 8 and about 20 wt. %; and a borax content ranging between about 4 and about 7 wt. % preferably between about 4.5 and about 6 wt. %.

The controlled-release pesticide compositions of the invention are useful in agricultural applications for controlling or eliminating a wide variety of pests such as rice flies, e.g. *Stitophilus zeamais,* sugar cane wire worm, and the sweet potato pest *Cylas formicarius.* To treat areas infested by one or more pests, the controlled-release pesticide composition of the invention containing at least one or more pesticides, is administered by any suitable conventional method in any suitable amounts effective to control or kill the pests.

The present invention will be substantially illustrated in the following examples, but the scope of the present invention should not be limited by these examples.

EXAMPLE 1

Allethrin Encapsulation in a Polymer Matrix of Starch-borax-urea

A suspension of 46 g of tapioca starch and 10 g of allethrin in 70 g of water is agitated in a Waring blender at about 1500 rpm for a period of 10 minutes at 28° C. Thereafter, 10 g of urea is added to the mixture to gelatinize the starch.

The mixture is further agitated until the starch became gelatinized and the mixture becomes well dispersed. The temperature of the mixture reaches a temperature of 77° C. during the agitation process. Thereafter, 5 g of powdered borax is added into the dispersion and the borax-containing mixture is agitated for 10 minutes until a uniform rubbery mass forms.

The mass is then reduced into small particles by grinding, in the presence of 51 g of additional starch powder with the Waring blender, at high speed (about 1500 rpm), for 15 minutes at 40° C.

The resultant particles is dried at 55° C. for 24 hours. The particles has a mesh size ranging between 10 and 60, and a water content of 12.5 wt. %.

The constituents of this formulation (content 1) and other formulations (contents 2–4) prepared in the same manner, but having different amounts of urea, are listed in Table 1 below.

TABLE 1

| | Allethrin encapsulated in starch-borax-urea matrix | | | |
|---|---|---|---|---|
| FORMULA | CONTENT 1 | CONTENT 2 | CONTENT 3 | CONTENT 4 |
| Allethrin | 10 g | 10 g | 10 g | 10 g |
| Borax | 5 g | 5 g | 5 g | 5 g |
| The first starch for gelatinization | 46 g | 50 g | 50 g | 45 g |
| The second starch for grinding | 51 g | 42 g | 37 g | 37 g |
| Urea | 10 g | 15 g | 20 g | 25 g |

EXAMPLE 2

Evaluation of Release Rate of Various Formulations of Allethrin Encapsulated in a Starch-borax-urea Polymer Matrix This Example provides an evaluation of the release rates of the allethrin encapsulated polymer matrix formulations described in Table 1 in Example 1.

One gram of the polymer-matrix type pesticide was suspended in 100 ml water for 28 days at room temperature in order to analyze the release rate in water. At the end of 28 days, the amount of pesticide contained in the water was measured by HPLC. The results are summarized in Table 2. Table 2 shows that the polymer matrix type pesticides of the present invention can be prepared having varying pesticide release rates and that when the urea content in the compositions increases, the release rate decreases.

TABLE 2

The release rates of Allethrin in a polymer matrix of starch-borax-urea

| RELEASE RATE | CONTENT 1 | CONTENT 2 | CONTENT 3 | CONTENT 4 |
|---|---|---|---|---|
| (mg Allethrin/ day-g polymer matrix) | 0.1281 | 0.1133 | 0.0938 | 0.0713 |

EXAMPLE 3

Evaluation of the Release Rate of Various Formulations of Fenvalerate Encapsulated in a Starch-borax-urea Polymer Matrix Table 3 summarizes the content of various formulations of fenvalerate encapsulated in a polymer matrix of starch-borax-urea. The fenvalerate formulations were prepared in the same manner described in Example 1. One gram of the polymer-matrix type pesticide was suspended in 100 ml water for 34 days in order to analyze the release rate in water. At the end of 34 days, the amount of fenvalerate in the water was measured by HPLC. The results, shown in Table 4, demonstrate that when the amount of urea in the formulations increase, the release rates also decrease.

TABLE 3

Formulations of fenvalerate encapsulated in polymer matrix of starch-borax-urea

| FORMULA | CONTENT 1 | CONTENT 2 | CONTENT 3 |
|---|---|---|---|
| Fenvalerate | 10 g | 10 g | 10 g |
| Borax | 5 g | 5 g | 5 g |
| The first starch for gelatinization | 42 g | 42 g | 42 g |
| The second starch for grinding | 50 g | 45 g | 40 g |
| Urea | 15 g | 20 g | 25 g |

TABLE 4

The release rate of Fenvalerate encapsulated in polymer matrix of starch-borax-urea

| RELEASE RATE | CONTENT 1 | CONTENT 2 | CONTENT 3 |
|---|---|---|---|
| (mg Fenvalerate/ day-g polymer matrix) | 0.0735 | 0.058 | 0.051 |

EXAMPLE 4

Evaluation of the Release Rate of Various Formulations of Carbofuran Encapsulated in a Starch-borax-urea Polymer Matrix Table 5 summarizes the content of various formulations of carbofuran encapsulated in a polymer matrix of starch-borax-urea. The carbofuran formulations were prepared in the same manner described in Example 1. One gram of the polymer-matrix type pesticide was suspended in 100 ml water for 42 days in order to analyze the release rate in water. At the end of 42 days, the amount of carbonfuran released into the water was measured by HPLC. These results are shown in Table 6 and demonstrate that polymer-matrix type pesticides having controllable pesticide release rates are obtainable. Moreover, the results show that when the amount of urea in the formulations increase, the pesticide release rates decrease.

TABLE 5

The formulations of carbofuran encapsulated in polymer matrix of starch-borax-urea

| FORMULA | CONTENT 1 | CONTENT 2 | CONTENT 3 |
|---|---|---|---|
| Carbofuran | 6 g | 6 g | 6 g |
| Borax | 5 g | 5 g | 5 g |
| The first starch for gelatinization | 42 g | 42 g | 42 g |
| The second starch for grinding | 50 g | 45 g | 40 g |
| Urea | 15 g | 20 g | 25 g |

TABLE 6

The release rates of carbofuran encapsulated in polymer matrix of starch-borax-urea

| RELEASE RATE | CONTENT 1 | CONTENT 2 | CONTENT 3 |
|---|---|---|---|
| (mg Carbofuran/ day-g polymer matrix) | 0.4535 | 0.4134 | 0.4084 |

EXAMPLE 5

Efficacy Evaluation of Deltamethrin Encapsulated in a Starch-borax-urea Polymer Matrix In this Example, two polymer matrix formulations of the starch-borax-urea type having 1.17 wt. % (formula I) and 1.85 wt. % (formula II) deltamethrin were used to test their effects on the mortality of *Stitophilus zeamais*, a rice pest. The constituents of these deltamethrin formulations are shown in Table 7. These formulations were prepared in the same manner as described in Example 1.

TABLE 7

The formulations of deltamethrin encapsulated in polymer matrix of starch-borax-urea

| FORMULA | I | II |
|---|---|---|
| Deltamethrin | 10 g | 20 g |
| Borax | 5 g | 5 g |
| The first starch for gelatinization | 30 g | 30 g |
| The second starch for grinding | 45 g | 45 g |
| Urea | 5 g | 5 g |

Formulas I and II were independently and uniformly mixed (1 g pesticide formulation per 1000 g of rice) with rice grains (250 g) in triplicate. One hundred rice pests were then added to each mixture. A blank test (control) containing no pesticide was also included in the evaluation. The results (% pests killed) of the evaluation are shown in Table 8. Table 8 shows that the deltamethrin's polymer-matrix types of starch-borax-urea control the release rate of the pesticide. The mortality of the rice pest is very high after 21 months.

TABLE 8

The effect on the mortality rate of *Stitophilus zeamais* on rice grain by exposure to formulations of deltamethrin encapsulated in a starch-borax-urea polymer matrix.

| Formula | Release Rate (mg/day) | 0 Month | 1st Month | 3rd Month | 6th Month | 15th Month | 21st Month |
|---|---|---|---|---|---|---|---|
| Formula I (1.17 wt. %) | 61 | 90.1$^b$ | 100$^a$ | 99.8$^a$ | 99.9$^a$ | 97.2$^b$ | 88.0$^a$ |
| Formula II (1.84 wt. %) | 214 | 95.1$^b$ | 96.7$^b$ | 100$^a$ | 100$^a$ | 98.3$^{ab}$ | 85.0$^a$ |
| Blank Test | — | 0.8$^d$ | 2.5$^d$ | 29.75$^c$ | 1.1$^c$ | 4.4$^d$ | 6.3$^c$ |

Note: This test uses Duncan's multivariance analysis at $p \leq 0.05$. Where the superscript letter in different columns are not the same, the difference between the values are statistically significant.

What is claimed is:

1. A particulate controlled-release pesticide composition having an oil-soluble pesticide encapsulated in a starch-borax-urea matrix, wherein said composition contains about 1 to 25 wt. % of pesticide; about 50 to 80 wt. % of starch; about 4 to 25 wt. % of urea; and about 4 to 7 wt. % of borax; and wherein, the greater the ratio of the urea to starch in said matrix, the lower the release rate of said pesticide, wherein said pesticide is allethrin, carbofuran, fenvalerate, deltamethrin, cypermethrin, chloropyrifos, diazinon or permethrin.

2. The composition according to claim 1, wherein said composition has a particle mesh size of from about 10 to 60.

3. A method for treating an area infested with a pest comprising administering the particulate controlled release pesticide composition of claim 1 to said area in an amount effective to control or kill said pest.

* * * * *